(12) United States Patent
Chen et al.

(10) Patent No.: US 8,974,840 B2
(45) Date of Patent: Mar. 10, 2015

(54) MILK-FERMENTED PRODUCT AND USE THEREOF

(71) Applicant: National Chung Hsing University, Taichung (TW)

(72) Inventors: Chuan-Mu Chen, Tiachung (TW); Hsiao-Ling Chen, Taichung (TW)

(73) Assignee: National Chung Hsing University, Taichung (TW)

( * ) Notice: Subject to any disclaimer, the term of this patent is extended or adjusted under 35 U.S.C. 154(b) by 0 days.

(21) Appl. No.: 14/327,231

(22) Filed: Jul. 9, 2014

(65) Prior Publication Data
US 2014/0378386 A1 Dec. 25, 2014

Related U.S. Application Data

(63) Continuation-in-part of application No. 13/661,080, filed on Oct. 26, 2012, now abandoned.

(30) Foreign Application Priority Data

Jul. 10, 2012 (TW) .............................. 101124838 A

(51) Int. Cl.
*A01N 65/00* (2009.01)
*C07K 2/00* (2006.01)
*A23C 9/12* (2006.01)

(52) U.S. Cl.
CPC .... *C07K 2/00* (2013.01); *A23C 9/12* (2013.01)
USPC ....................................................... 424/725

(58) Field of Classification Search
None
See application file for complete search history.

(56) References Cited

U.S. PATENT DOCUMENTS

2009/0196867 A1 * 8/2009 Kubow .......................... 424/116

* cited by examiner

*Primary Examiner* — Michael Meller
(74) *Attorney, Agent, or Firm* — Ming Chow; Sinorica, LLC

(57) ABSTRACT

The present invention discloses a novel milk-fermented product comprising a group of peptides. The peptides are composed from no. 1 to no. 7 of the figure that is selected from the group consisting of FIG. 11 to FIG. 18. And the novel milk-fermented product is used for suppressing the reduction of bone mineral density. Therefore, the novel milk-fermented product could be a component of foods, nutrient supplement or medicine for treating or preventing osteoporosis.

1 Claim, 20 Drawing Sheets

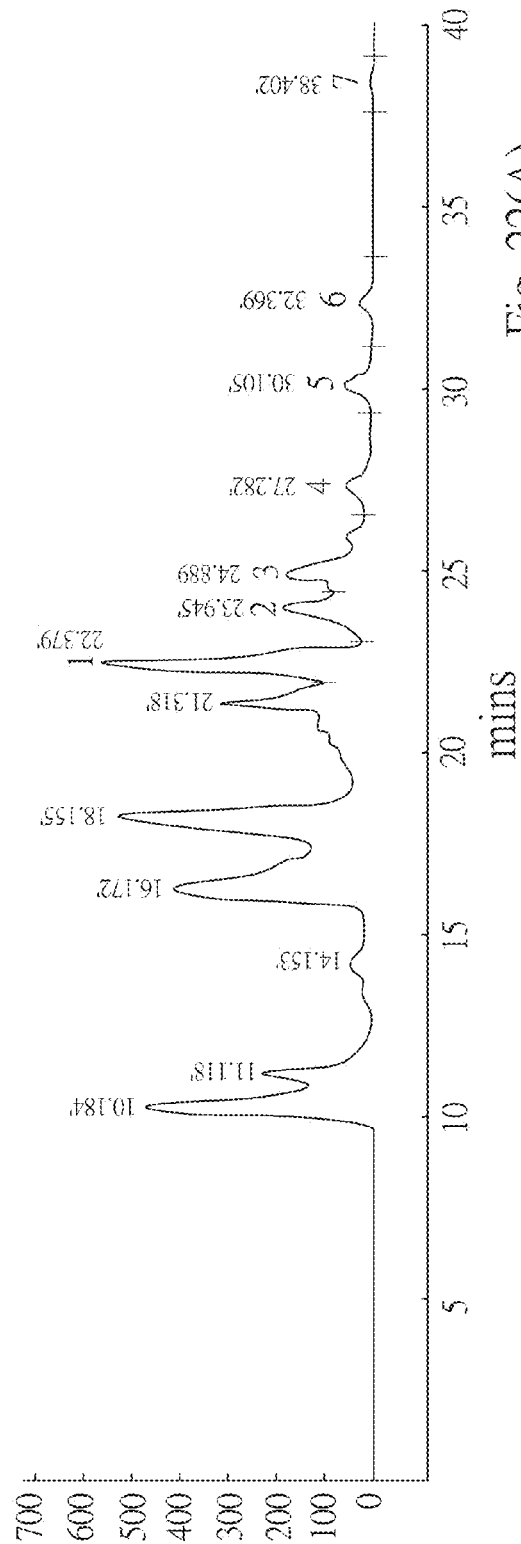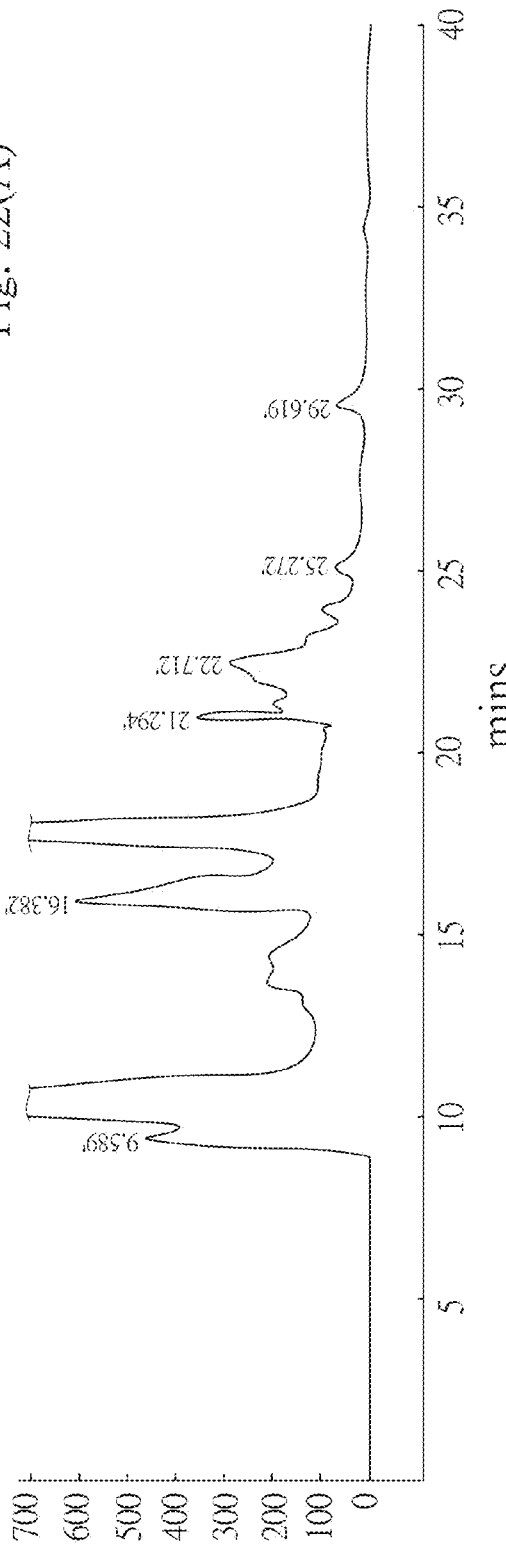

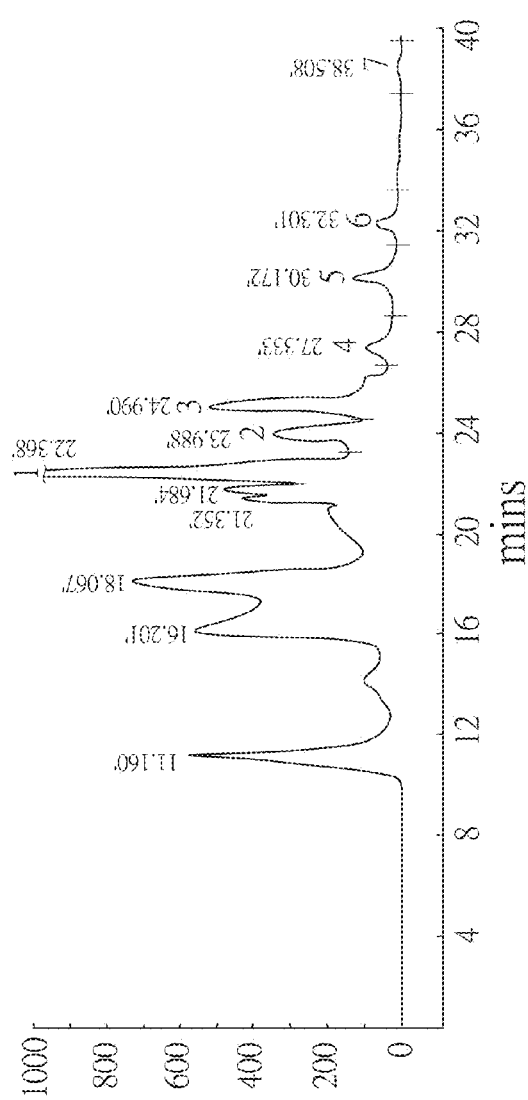
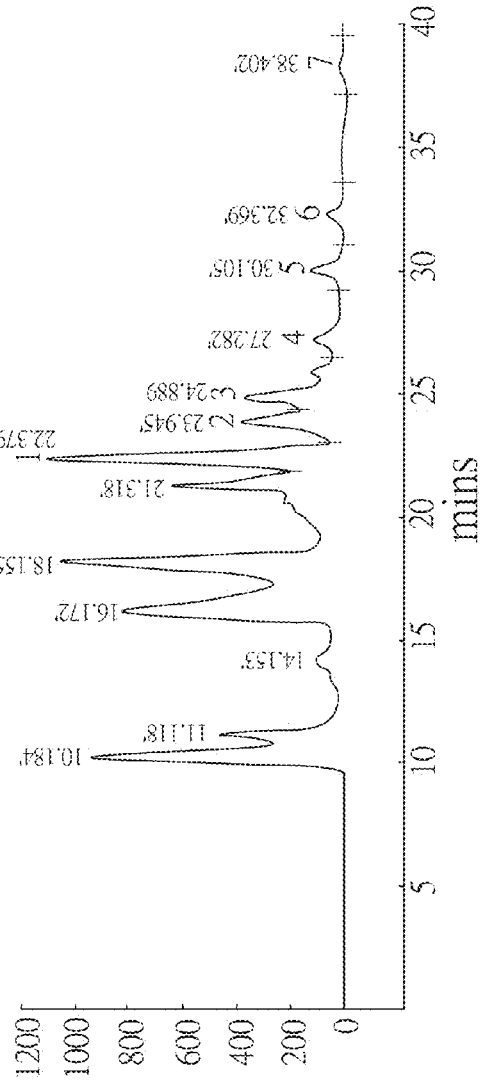
Fig. 24(A)
Fig. 24(B)

MILK-FERMENTED PRODUCT AND USE THEREOF

This application is a continuation-in-part of U.S. patent application Ser. No. 13/661,080 filed on Oct. 26, 2012 which claimed a foreign priority to TW 101124838, filed on Oct. 7, 2012.

FIELD OF THE INVENTION

The present invention relates to a bioactive peptide, especially a novel milk-fermented product and use thereof.

BACKGROUND OF THE INVENTION

Since the global population structure is leading to an aging population in society, elderly people not only have to face the threats of cancer, stroke and myocardial infraction, but must also pay more attention to osteoporosis. In detail, the bone mass of the human body keeps growing after birth and reaches the maximum by age 30. After age 30, bone mass decreases every year. This especially applies to postmenopausal women, whose bone mass decreases dramatically due to the reduction of estrogen, which can induce the formation of bone mass. Moreover, in patients with osteoporosis, bones become loose and brittle, and the risk of fracture is increased. Elderly people especially may suffer fractures of the neck or thighbone by falling down, further leading to often lumbago and disability, and the bone fractures are very hard to be cured. According to statistics in Taiwan, the probability for osteoporosis fracture is about two to four times higher than the probability for stroke. The incidence of osteoporosis fracture is estimated to increase six times globally by 2050, especially in Asia. The 2009 report from the Bureau of National Health Insurance in Taiwan suggests that the incidence of osteoporosis in Taiwan among postmenopausal women is about 25% and at least 20% of men also suffer from this disease. Furthermore, the report also reveals that approximately 10~20% of patients who experience a hip fracture will die in the first year following the fracture. This mortality rate is almost the same as with the late phase of breast cancer. In addition, 50% of osteoporosis patients cannot live independently, and 20~25% of osteoporosis patients cannot act alone. Therefore, the health care system and society have to spend a lot of social and medical resources. Thus, this is an important research issue for the prevention and health care of osteoporosis.

In osteoporosis, the major factor causing fractures depends on the bone mineral density. Thus, the goal of treatment is to reduce bone loss or to increase bone mass and density. As of now, there are several drugs that can reduce the loss of bone mass by decreasing bone resorption, such as Calcitonin, hormone therapy and bisphosphonate. In addition, anabolic drugs, such as parathyroid hormone (PTH) can stimulate osteoblasts to increase bone formation (Riggs and Melton, 1988). Although these two kinds of drugs have been used for curing patients with osteoporosis, there still exist the following problems. First, these drugs cannot be used on people over 30 years old and those whose bone masses are reducing but do not meet the standard of osteoporosis. Second, treatments with bisphosphonate have the side effect of osteonecrosis of the jaw in patients. In order to avoid the drawbacks above, there are many nutriments for calcium supply on the market to prevent bone loss and to supply calcium nutrition in bone. However, the nutriments neither have effects on the control of bone loss, nor supply bone calcium by inefficient calcium absorption.

Recently, research on the bioactive peptides in natural products has rapidly developed. Some reports suggest that many milk-derived peptides have physiological activities, such as antihypertensive, opioid-like, immunomodulating, antithrombotic, antimicrobial and calcium-absorption enhancing properties (Zinn, 1988; Yamamoto, 1998; Shan, 2000). Thus, the researches all focus on discovering the protein from natural products that can improve osteoporosis. Furthermore, these peptides with different physiological activities in natural products do not have side effects such as those caused by chemical drugs. However, most bioactive peptides, including ACE inhibitory peptides, antimicrobial peptides and antihypertensive peptides, have to be processed into oligo-peptides by enzymatic reaction in order to have full the functions of the physiological activities (Meisel, 1999). In addition, fermented or non-fermented foods also can improve its function by proper hydrolysis (Vermeirssen et al., 2003; Hernandez-Ledesma et al., 2004).

Thus, how to obtain small-molecule peptides with physiological activities from natural products and further specifically improve the symptoms of osteoporosis are important issues in the biomedical and pharmacological fields.

SUMMARY OF THE INVENTION

In one of its aspects, the invention provides a novel milk-fermented product that at least has a peptide group, wherein the peptide group comprises peaks of reference number 1 to 7 shown in any one of FIG. 11 to FIG. 18. The novel milk-fermented product with an effect of decreased bone density loss on organisms can be further applied to foods, nutriments and medical products to prevent or cure osteoporosis and supply bone nutrition.

Furthermore, the novel milk-fermented product is derived from an animal milk that in a certain fermentation condition undergoes fermentation of kefir grains or at least one strain isolated from kefir grains, wherein the animal milk may be obtained from cattle, goats, sheep, pigs or horses.

Another aspect of the invention provides a nutriment that at least comprises a peptide group and a certain nutrient ingredient, wherein the peptide group comprises peaks of reference number 1 to 7 shown in any one of FIG. 11 to FIG. 18, and the certain nutrient ingredient, which will be a mineral element, such as calcium ion.

The other aspect of the invention is to provide a food, such as a yogurt beverage, that at least comprises a food ingredient and a peptide group, wherein this peptide group comprises peaks of reference number 1 to 7 shown in any one of FIG. 11 to FIG. 18.

One another aspect of the invention is to provide a medical compound for treating osteoporosis by orally administrated that at least comprises an effective ingredient and a medically acceptable carrier and/or excipient, wherein the effective ingredient is a peptide group including peaks of reference number 1 to 7 shown in any one of FIG. 11 to FIG. 18.

In another aspect, the invention is also to provide a medical compound for prevent bone mineral density loss by orally administrated that at least comprises an effective ingredient and a medically acceptably carrier and/or excipient, wherein the effective ingredient is a peptide group including peaks peaks of reference number 1 to 7 shown in any one of FIG. 11 to FIG. 18.

BRIEF DESCRIPTION OF THE DRAWINGS

FIG. 22A shows the FIG. 12.
FIG. 22B shows the FIG. 21.

FIG. 24A shows the FIG. 23.
FIG. 24B shows the FIG. 12.

DETAILED DESCRIPTION OF THE INVENTION

The present invention discloses a novel milk-fermented product.

According to one embodiment of the present invention, the novel milk-fermented product derived from an animal milk that undergoes fermentation of kefir grains or strains isolated from kefir grains, at least including a peptide group, wherein the peptide group comprises peaks of reference number 1 to 7 shown in any one of FIG. 11 to FIG. 18. Furthermore, by fermentation reaction, the big molecule proteins in the animal milk can be efficiently processed into the small fragmented peptides such as the peaks of reference number 1 to 7 shown in any one of FIG. 11 to FIG. 18, and the each small fragmented peptide has never been discovered from non-fermented animal milk.

According to previous studies, the strains isolated from kefir grains include lactic acid bacteria and yeasts, wherein lactic acid bacteria more include *Lactobacillus, Lactococcus, Streptococcus, Leuconostoc* and *Acetobacter*, and yeasts more include *Saccharomyces, Candida, Kluyveromyces, Issatchenkia, Pichia* and *Torulopsis*.

According to other embodiments of the present invention, the novel milk-fermented product has positive effects such as improvement of osteoporosis, prevention of bone mineral density loss and enhancement of calcium absorption.

Therefore, the novel milk-fermented product may be applied in organisms, and also may be obtained the peptide group such as the peaks of reference number 1 to 7 shown in any one of FIG. 11 to FIG. 18 by purification and isolation. The peptide group may be a food ingredient, such as a fermented milk product; the peptide group may combine with a nutrient ingredient as a nutriment, such as a nutriment with calcium ion; the peptide group may be with at least one medically acceptable carrier and/or excipient to be fabricated to a medical compound by any traditional method for treating osteoporosis or preventing bone mineral density loss. Furthermore, the medical compound may be administered in different forms depending on the demands of oral delivery, such as granules, pills, pastille, powder, and liquid.

In order to clearly describe the present invention, the following non-limiting examples with figures are provided to further illustrate the present invention.

EXAMPLE 1

Preparation of the Novel Milk-Fermented Product

Use a certain volume of animal milk as a material milk that undergoes a fermentation reaction with a certain amount of kefir grains to produce a fermented milk, which is the novel milk-fermented product disclosed in the invention.

EXAMPLE 2

Examination of the Animal Model of Osteoporosis

In this example, plural C57BL/6J inbred female mice, which are purchased from National Taiwan University Laboratory Animal Center, are used.

Figure 1:
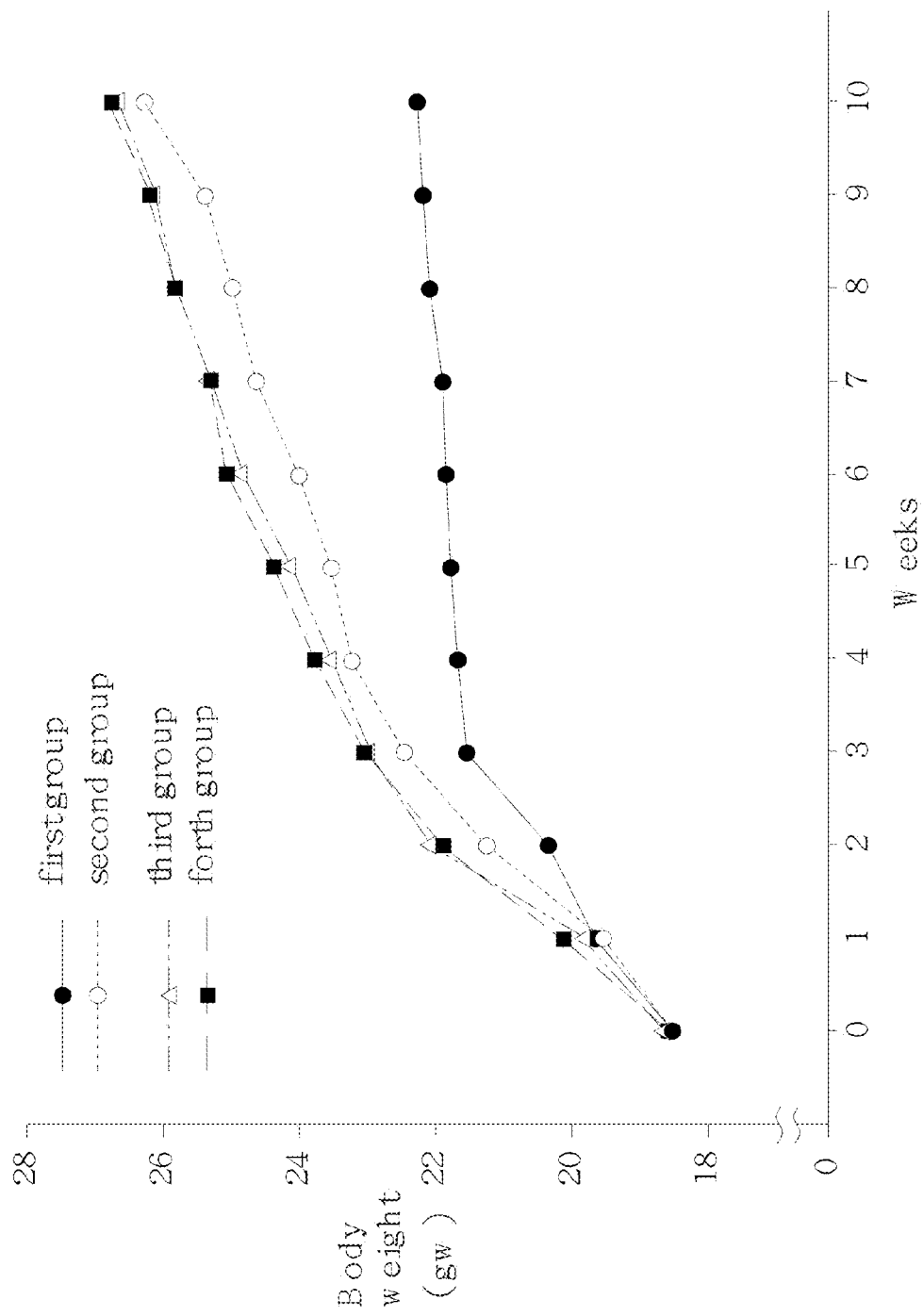
FIG. 1 shows the body weight curve of each mouse group in different weeks.

The 8-week-old mice that have undergone ovariectomy to mimic the postmenopausal mice with osteoporosis are further separated into three groups. In addition, there is another group in which the mice have undergone surgery without removing ovaries as a sham control. In this example, the first group is the sham control with normal food supply; the second group is the osteoporosis mice with normal food supply; the third group is the osteoporosis mice fed with the fermented milk; and the fourth group is the osteoporosis mice that are fed with fermented milk and additional calcium. The mice in each group are sacrificed after a certain amount of weeks, and the weekly weight changes of the mice in each group are shown in FIG. 1.

EXAMPLE 3

The Fermented Milk and the Fermented Milk with Additional Calcium Have the Activities of Improving Osteoporosis After sacrificing the mice from each group, the trabecular bones of the growth plate around the knees are examined by micro CT and electron microscope.

Figure 2A:
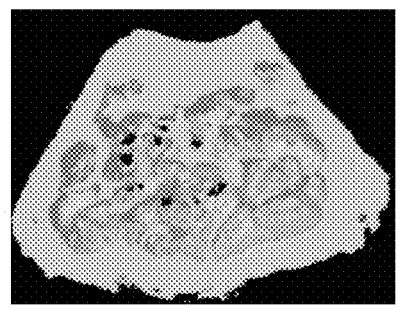
FIG. 2A shows the ∫g-CT scanning image of the cross section of the growth plate around the knees in the first group.
Figure 2B:
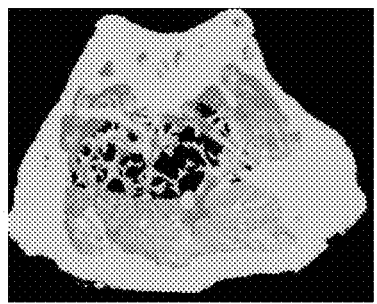
FIG. 2B shows the ∫g-CT scanning image of the cross section of the growth plate around the knees in the second group.
Figure 2C:
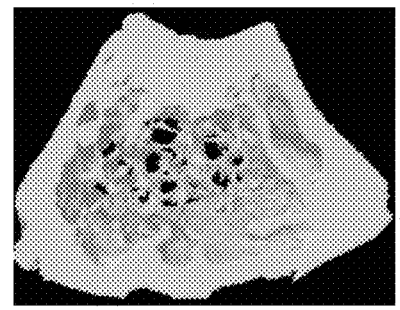
FIG. 2C shows the ∫g-CT scanning image of the cross section of the growth plate around the knees in the third group.
Figure 2D:
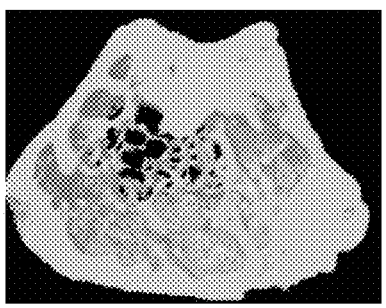
FIG. 2D shows the ∫g-CT scanning image of the cross section of the growth plate around the knees in the forth group.
Figure 3A:
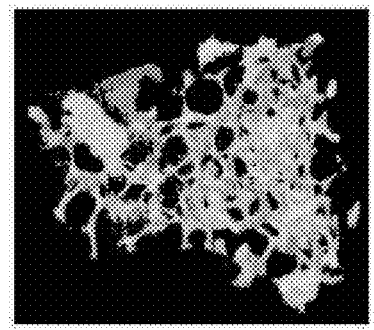
FIG. 3A shows the ∫g-CT scanning 3D image of the growth plate around the knees in the first group.
Figure 3B:
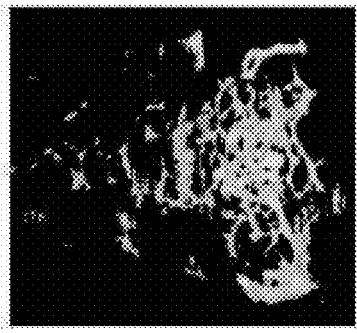
FIG. 3B shows the ∫g-CT scanning 3D image of the growth plate around the knees in the second group.
Figure 3C:
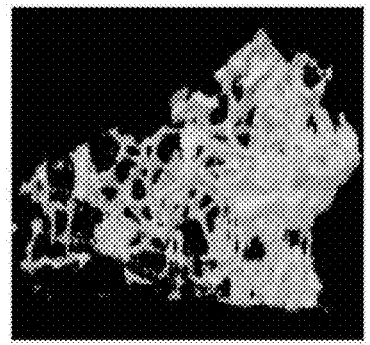
FIG. 3C shows the ∫g-CT scanning 3D image of the growth plate around the knees in the third group.
Figure 3D:
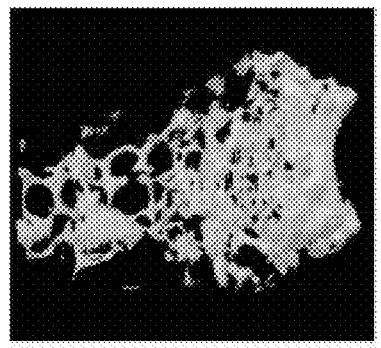
FIG. 3D shows the ∫g-CT scanning 3D image of the growth plate around the knees in the forth group.

The ]g-CT scanning images and ]g-CT scanning 3D images of the cross section of the growth plate around the knees in each mouse group are shown in FIG. 2 and FIG. 3 respectively, wherein the results of the first group are shown in FIG. 2A and FIG. 3A, the results of the second group are shown in FIG. 2B and FIG. 3B, the results of the third group are shown in FIG. 2C and FIG. 3C, and the results of the fourth group are shown in FIG. 2D and FIG. 3D.

Figure 4A:
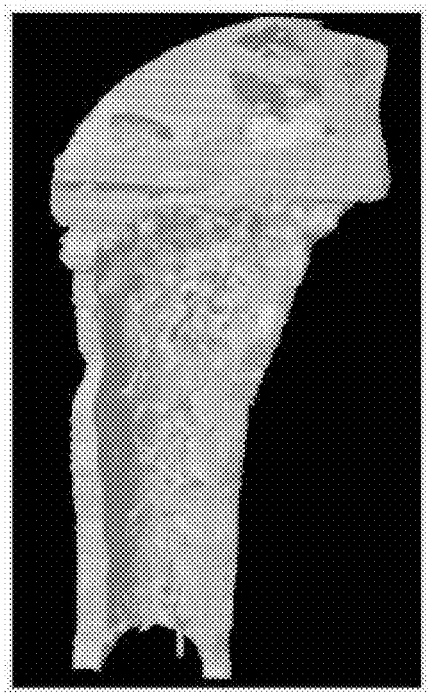
FIG. 4A shows the ∫g-CT scanning image of the vertical section of the growth plate around the knees in the first group.
Figure 4B:
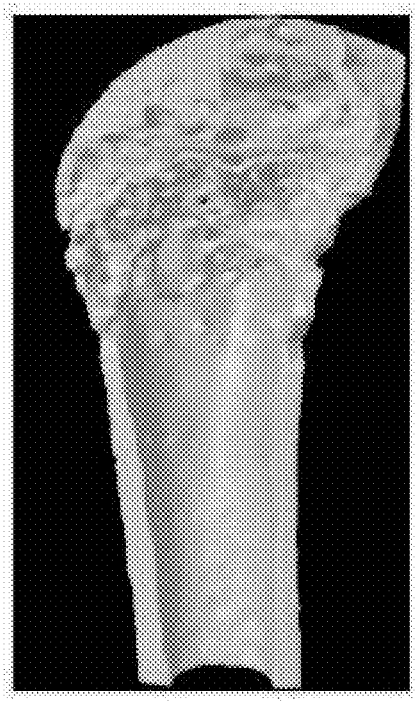
FIG. 4B shows the ∫g-CT scanning image of the vertical section of the growth plate around the knees in the second group.
Figure 4C:
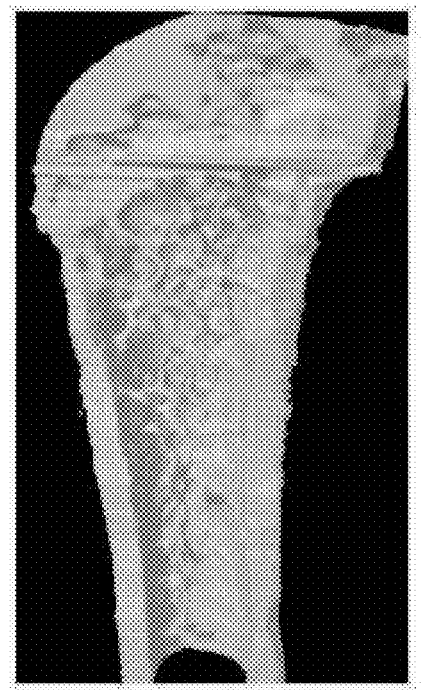
FIG. 4C shows the ∫g-CT scanning image of the vertical section of the growth plate around the knees in the third group.
Figure 4D:
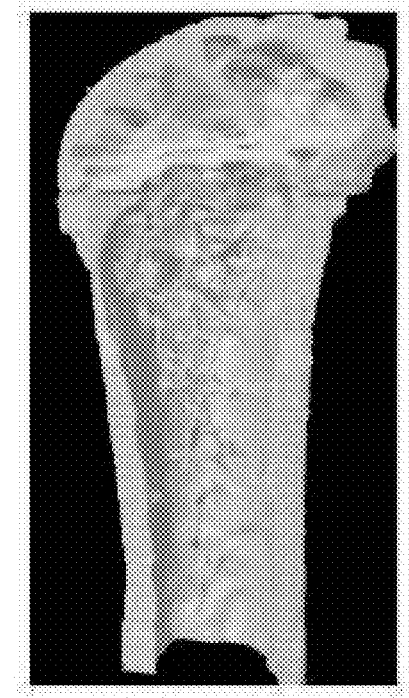
FIG. 4D shows the ∫g-CT scanning image of the vertical section of the growth plate around the knees in the forth group.
Figure 5A:
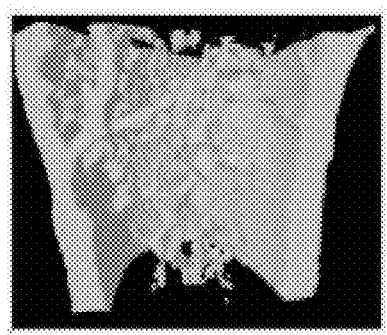
FIG. 5A shows the partial enlargement of FIG. 4A.
Figure 5B:
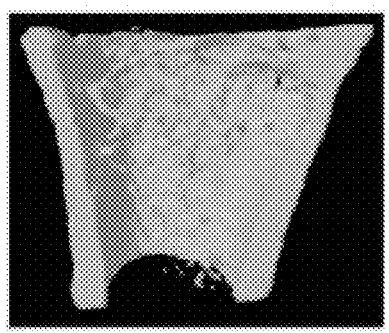
FIG. 5B shows the partial enlargement of FIG. 4B.
Figure 5C:
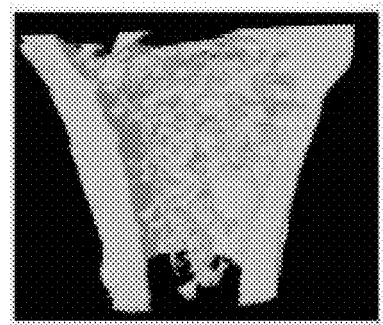
FIG. 5C shows the partial enlargement of FIG. 4C.
Figure 5D:
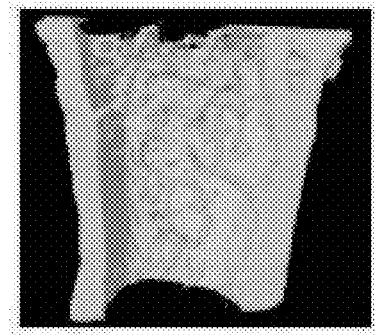
FIG. 5D shows the partial enlargement of FIG. 4D.

The ]g-CT scanning images and the high magnification ]g-CT scanning images of the vertical section of the growth plate around the knees in each mouse group are shown in FIG. 4 and FIG. 5 respectively, wherein the results of the first group are shown in FIG. 4A and FIG. 5A, the results of the second group are shown in FIG. 4B and FIG. 5B, the results of the third group are shown in FIG. 4C and FIG. 5C, and the results of the fourth group are shown in FIG. 4D and FIG. 5D.

Figure 6A:
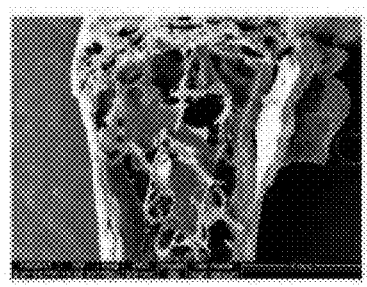
FIG. 6A shows the electron microscope scanning image of the vertical section of the growth plate around the knees in the first group.
Figure 6B:
FIG. 6B shows the electron microscope scanning image of the vertical section of the growth plate around the knees in the second group.
Figure 6C:
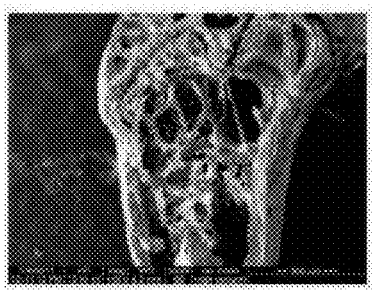
FIG. 6C shows the electron microscope scanning image of the vertical section of the growth plate around the knees in the third group.
Figure 6D:
FIG. 6D shows the electron microscope scanning image of the vertical section of the growth plate around the knees in the forth group.
Figure 7:
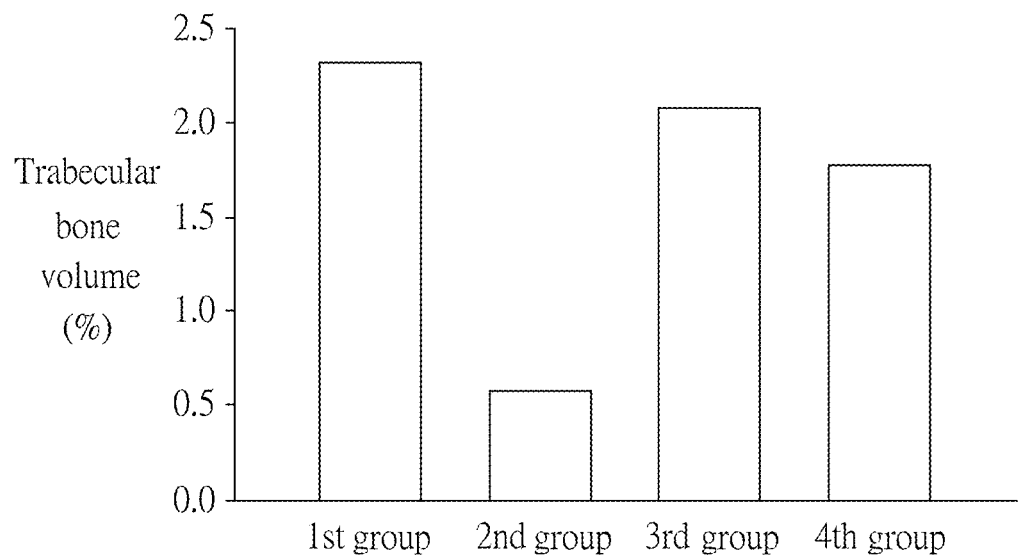
FIG. 7 shows the bar chart of the ratio of bone volume to total tissue volume of each mouse group.
Figure 8:
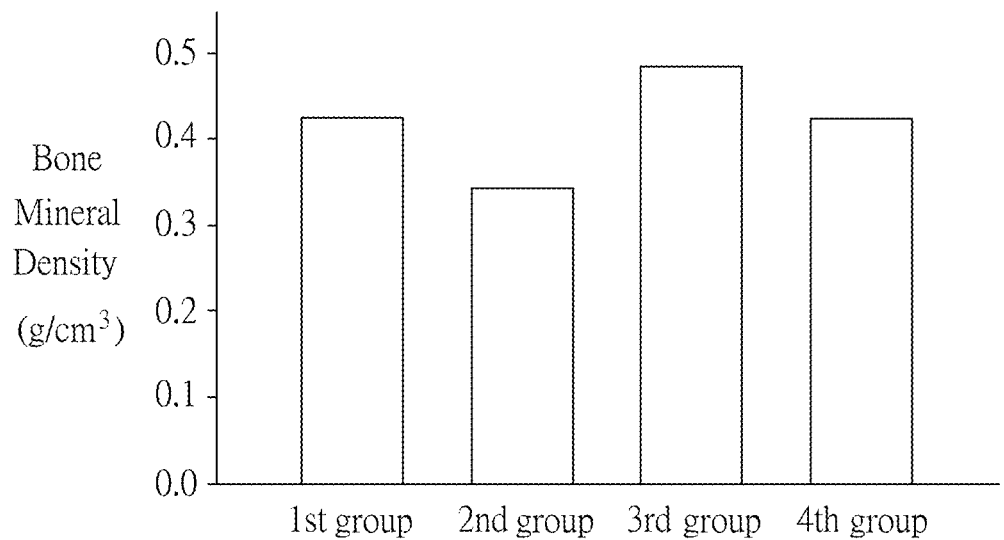
FIG. 8 shows the bar chart of the bone mineral density of each mouse group.
Figure 9:
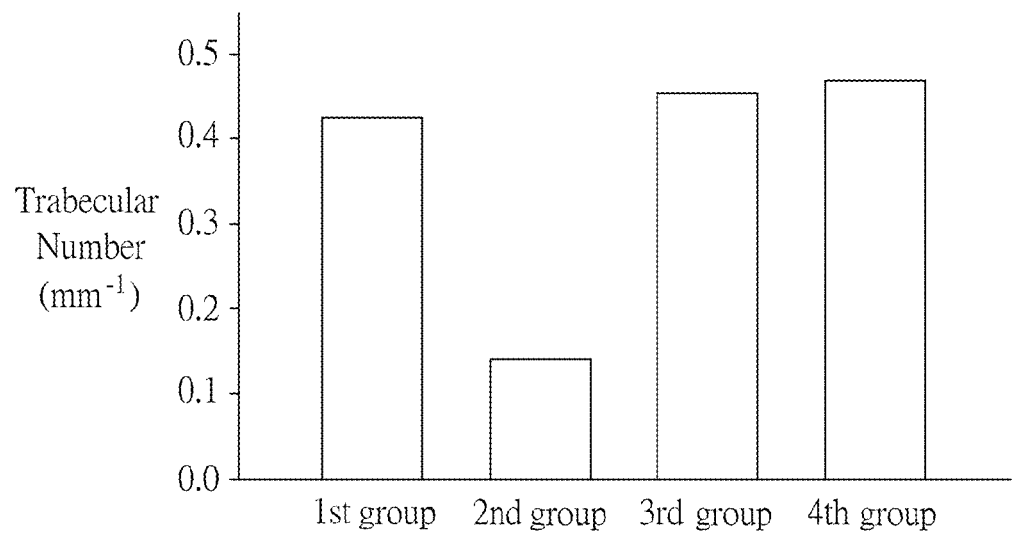
FIG. 9 shows the bar chart of the trabecular number of each mouse group.
Figure 10:
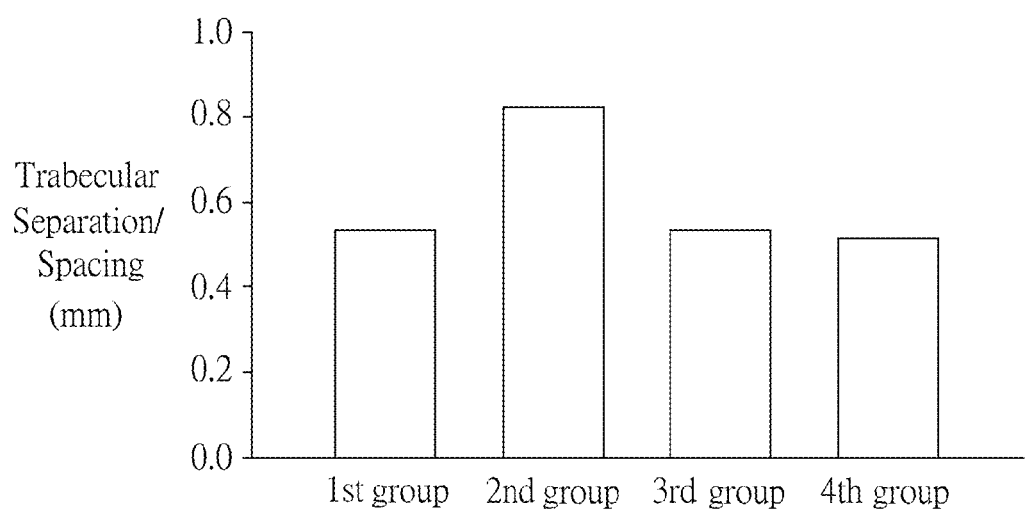
FIG. 10 shows the bar chart of the trabecular separation/spacing of each mouse group.

The electron microscope scanning images of the vertical section of the growth plate around the knees in each mouse group are shown in FIG. 6, wherein the result of the first group is shown in FIG. 6A, the result of the second group is shown in FIG. 6B, the result of the third group is shown in FIG. 6C, and the result of the fourth group is shown in FIG. 6D.

The results of FIG. 2 to FIG. 6 are further analyzed and calculated, and the statistic results, including the ratio of bone volume to total tissue volume, bone mineral density (BMD), trabecular number (Tb.N) and trabecular separation/spacing (Tb.Sp), are shown in FIG. 7 to FIG. 10 respectively.

According to the comparisons between FIG. 2 to FIG. 6, the second mouse group with normal food supply shows obviously loose bone structure and a lower trabecular number compared to the first mouse group. The bone structures of the third mouse group fed with fermented milk and the fourth mouse group fed with fermented milk and additional calcium show no difference compared with the first mouse group.

After further analyzing FIG. 7 to FIG. 10, it more obviously shows that the ratio of bone volume to total tissue volume, the bone mineral density and the trabecular number in second group are all significantly decreased, and the trabecular separation/spacing is increased. These all indicate severe bone mineral density loss, increased bone absorption and lost bone structure in the second mouse group. In comparison with the second mouse group, the ratio of bone volume to total tissue volume, the bone mineral density and the trabecular number are all significantly increased and the trabecular separation/spacing is effectively reduced in the third mouse group fed with fermented milk and the fourth mouse group fed with fermented milk and additional calcium. These results of the third and fourth mouse groups show no difference from the first mouse group.

Therefore, according to this example, we know that the fermented milk and the fermented milk with additional calcium indeed improve osteoporosis and increase bone mineral density.

EXAMPLE 4

Purification and Separation of the Fermented Milk

Each batch of the fermented milk from Example 1 is collected and further separated by HPLC with SEC columns under certain conditions: the determination wave length is 215 nm, elution buffer composed of 100 mM phosphoric acid aqueous, 1M sodium chloride and 1 mM EDTA pH6.5, and the flow rate is 0.5 ml/min.

The separation result by HPLC from each batch of the fermented milk is respectively as shown in FIG. 11 to FIG. 18. After comparing FIG. 11 to FIG. 18, it is found that each batch of the fermented milk can be separated into a peptide group such as the peaks of reference no. 1 to no. 7 shown in FIG. 11 to FIG. 18. In other words, it is indicated that the peptide group such as the peaks of reference no. 1 to no. 7 shown in any one of FIG. 11 to FIG. 18 is reproducible in the fermented milk.

Furthermore, the retention time for the peaks of reference no. 1 to no. 7 in each of FIG. 11 to FIG. 18 are shown as table 1.

TABLE 1

Figure 11:
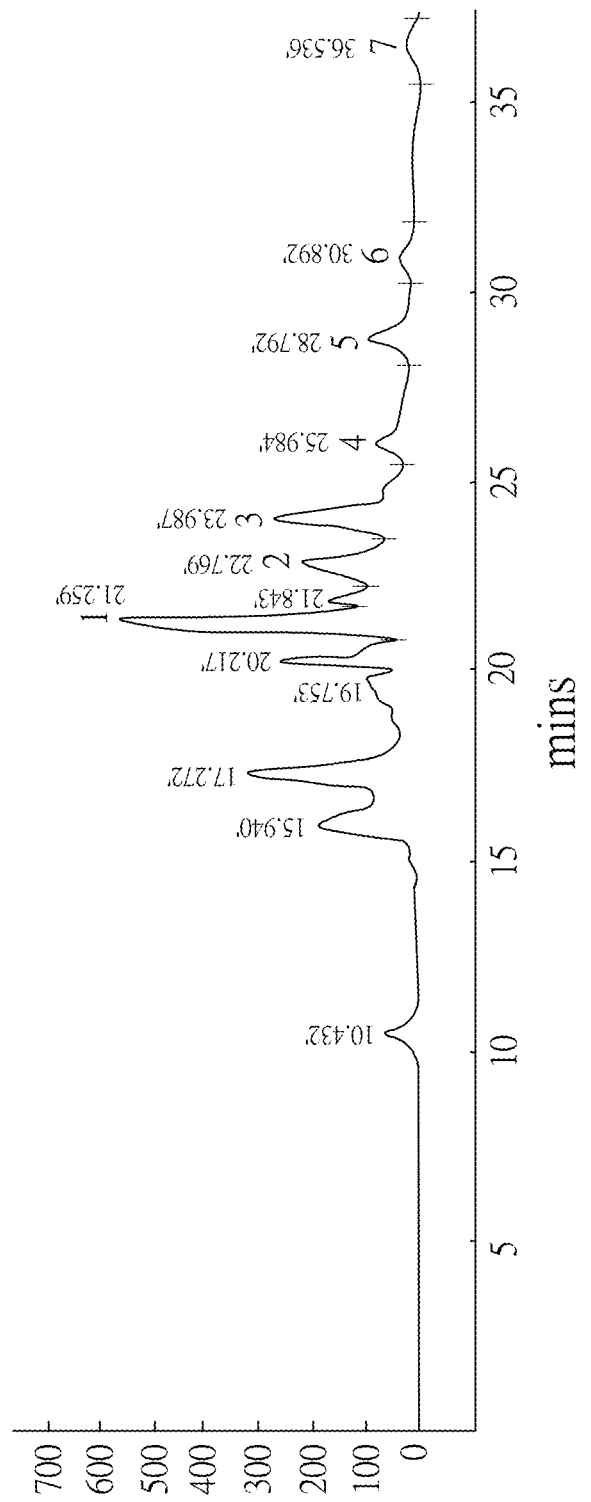
FIG. 11 shows the HPLC chromatogram of the first batch of fermented milk.
Figure 12:
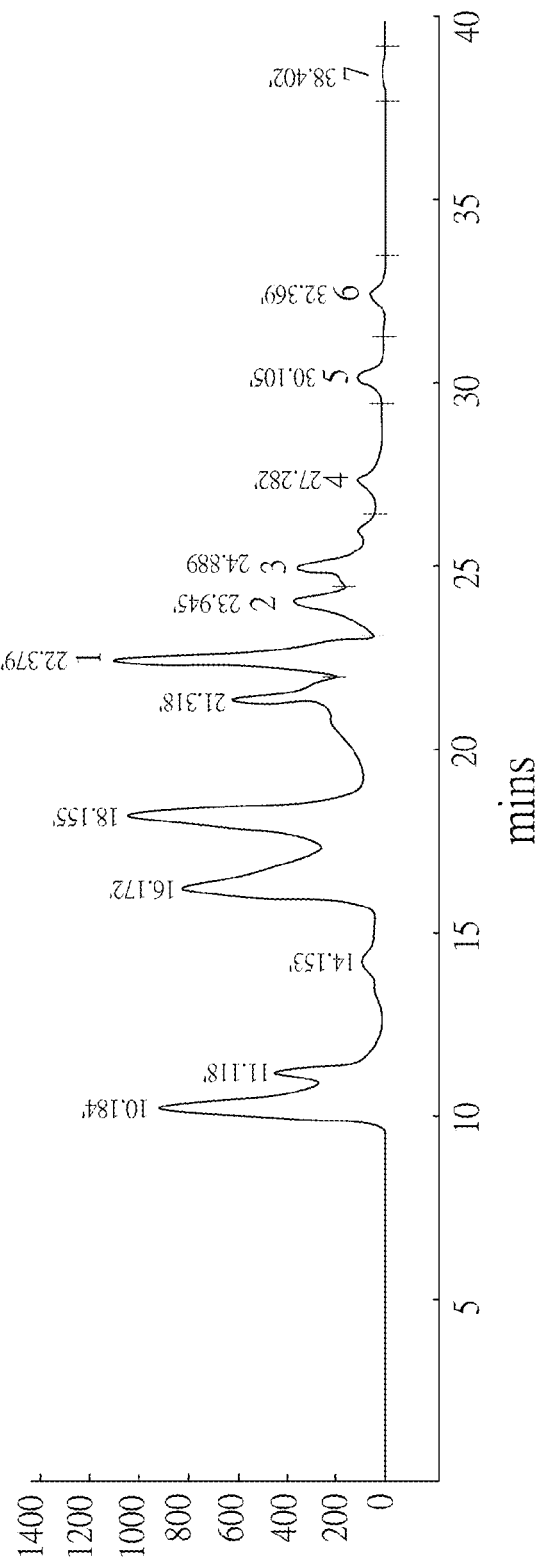
FIG. 12 shows the HPLC chromatogram of the second batch of fermented milk.
Figure 13:
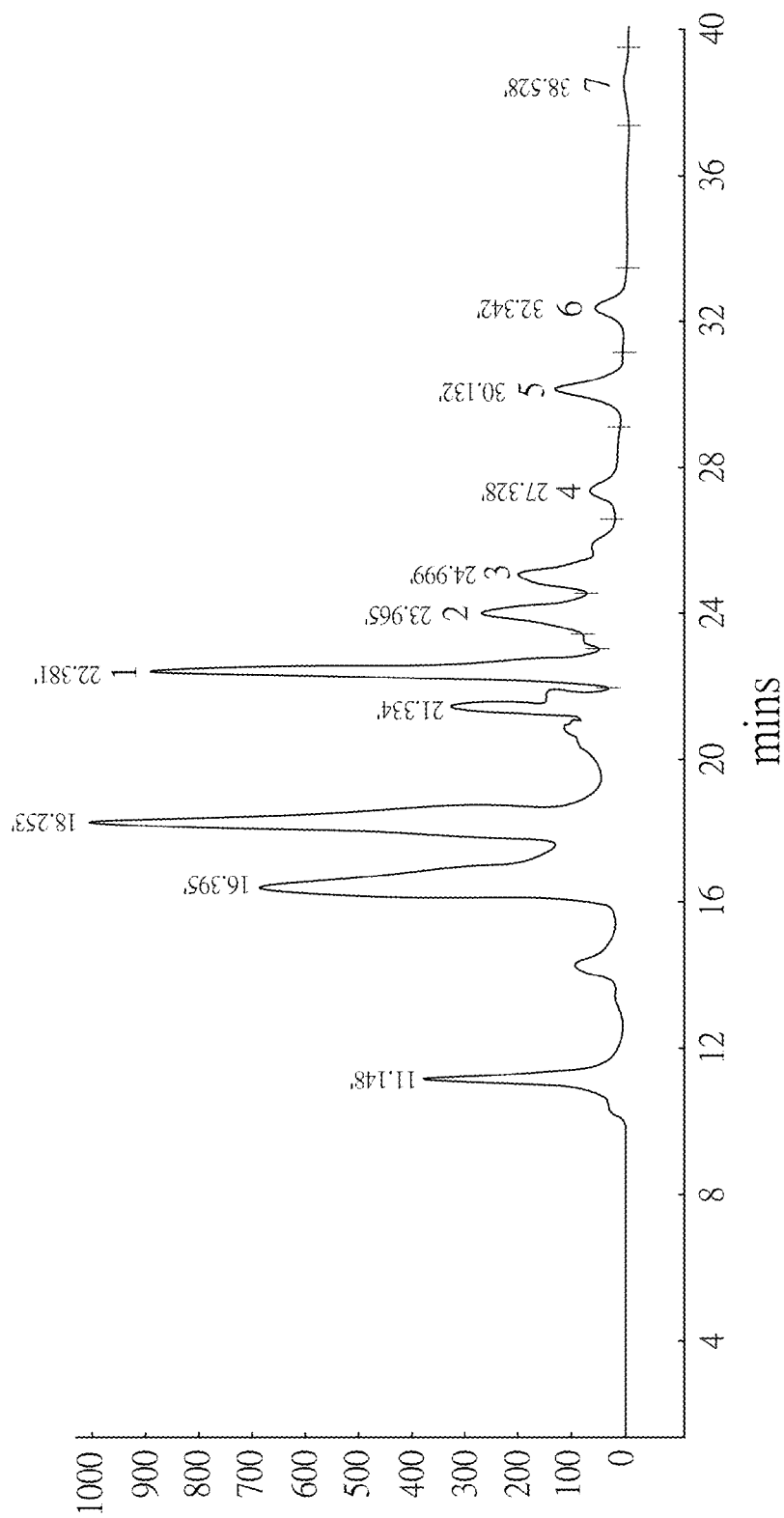
FIG. 13 shows the HPLC chromatogram of the third batch of fermented milk.
Figure 14:
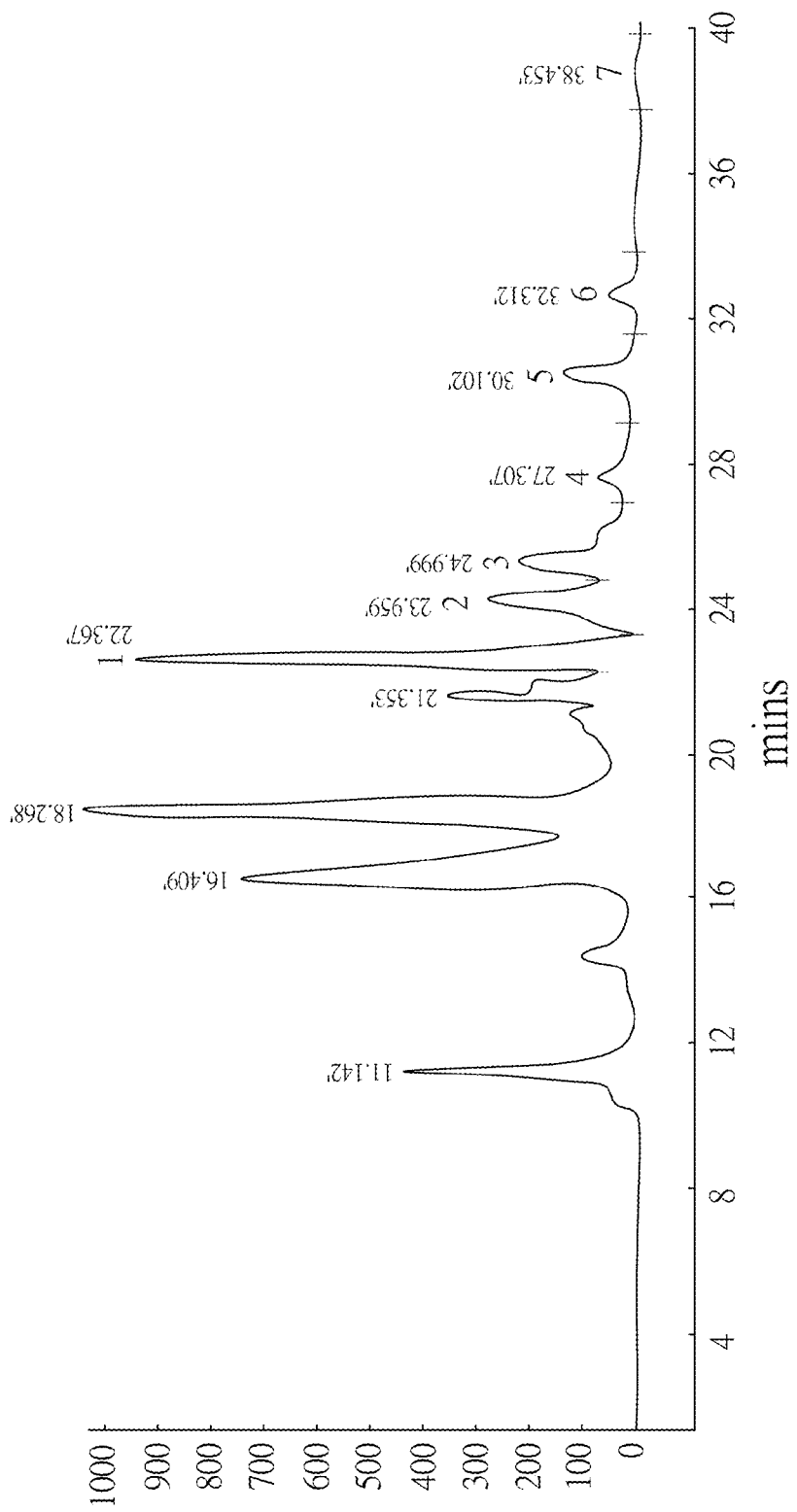
FIG. 14 shows the HPLC chromatogram of the forth batch of fermented milk.
Figure 15:
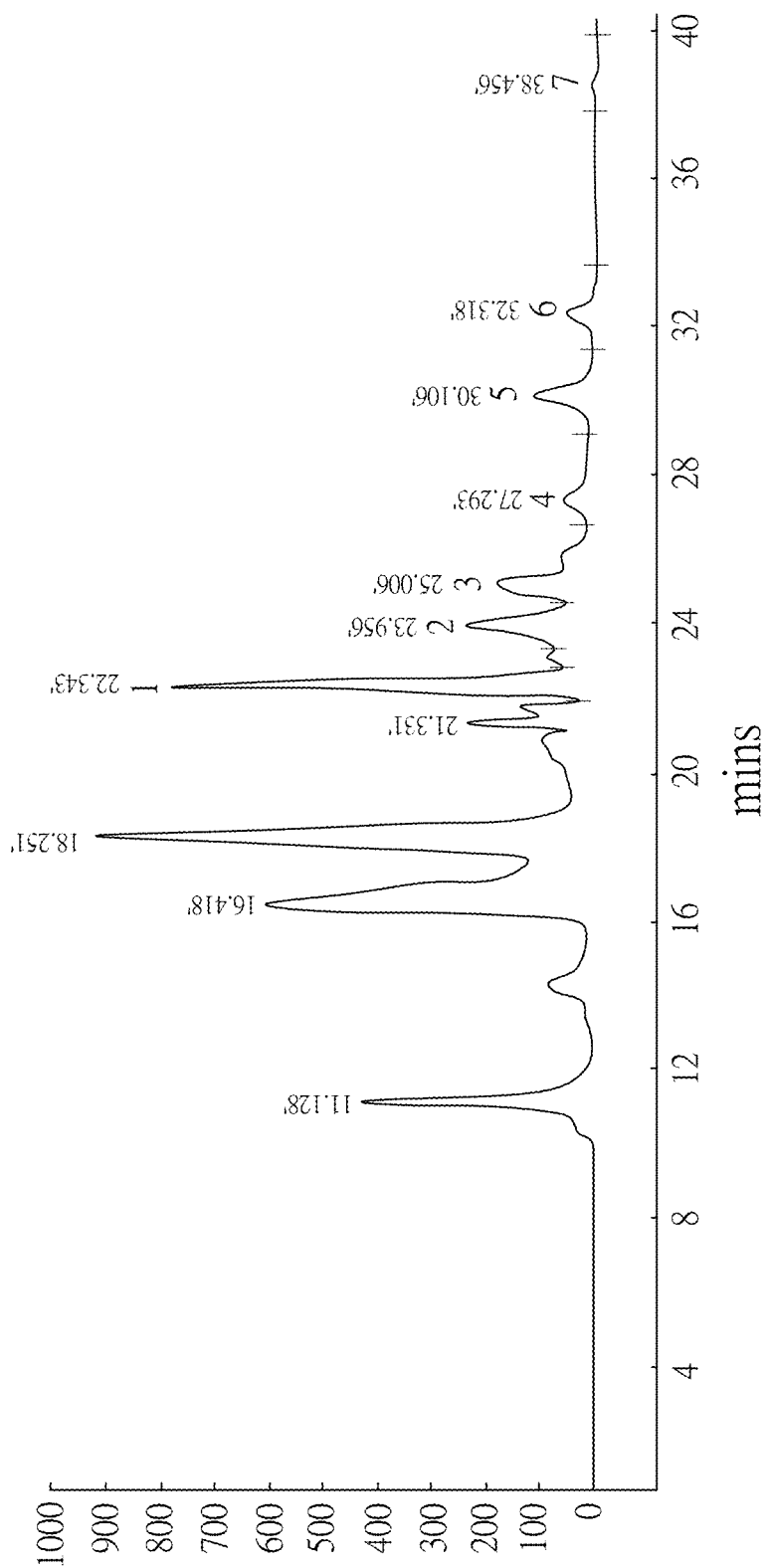
FIG. 15 shows the HPLC chromatogram of the fifth batch of fermented milk.
Figure 16:
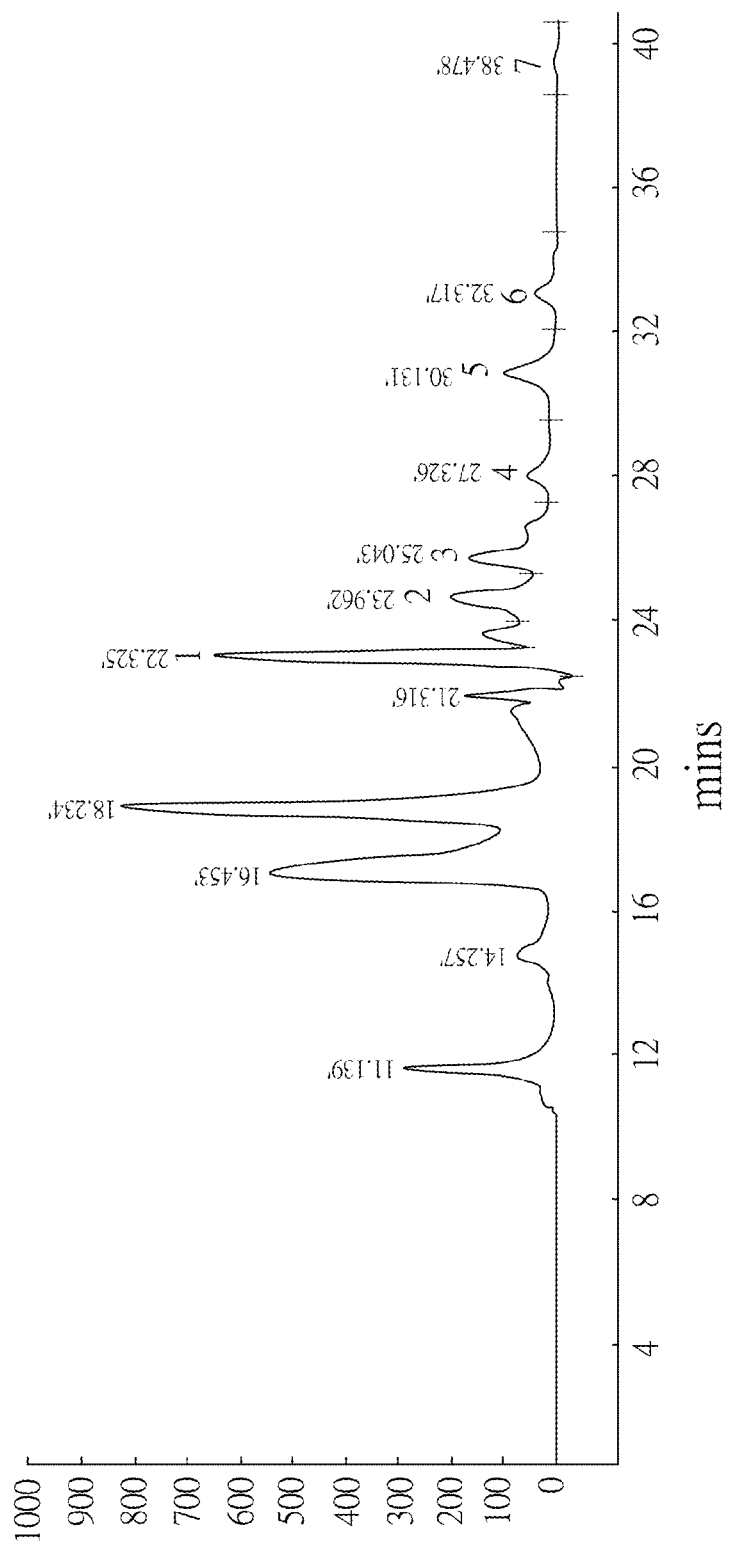
FIG. 16 shows the HPLC chromatogram of the sixth batch of fermented milk.
Figure 17:
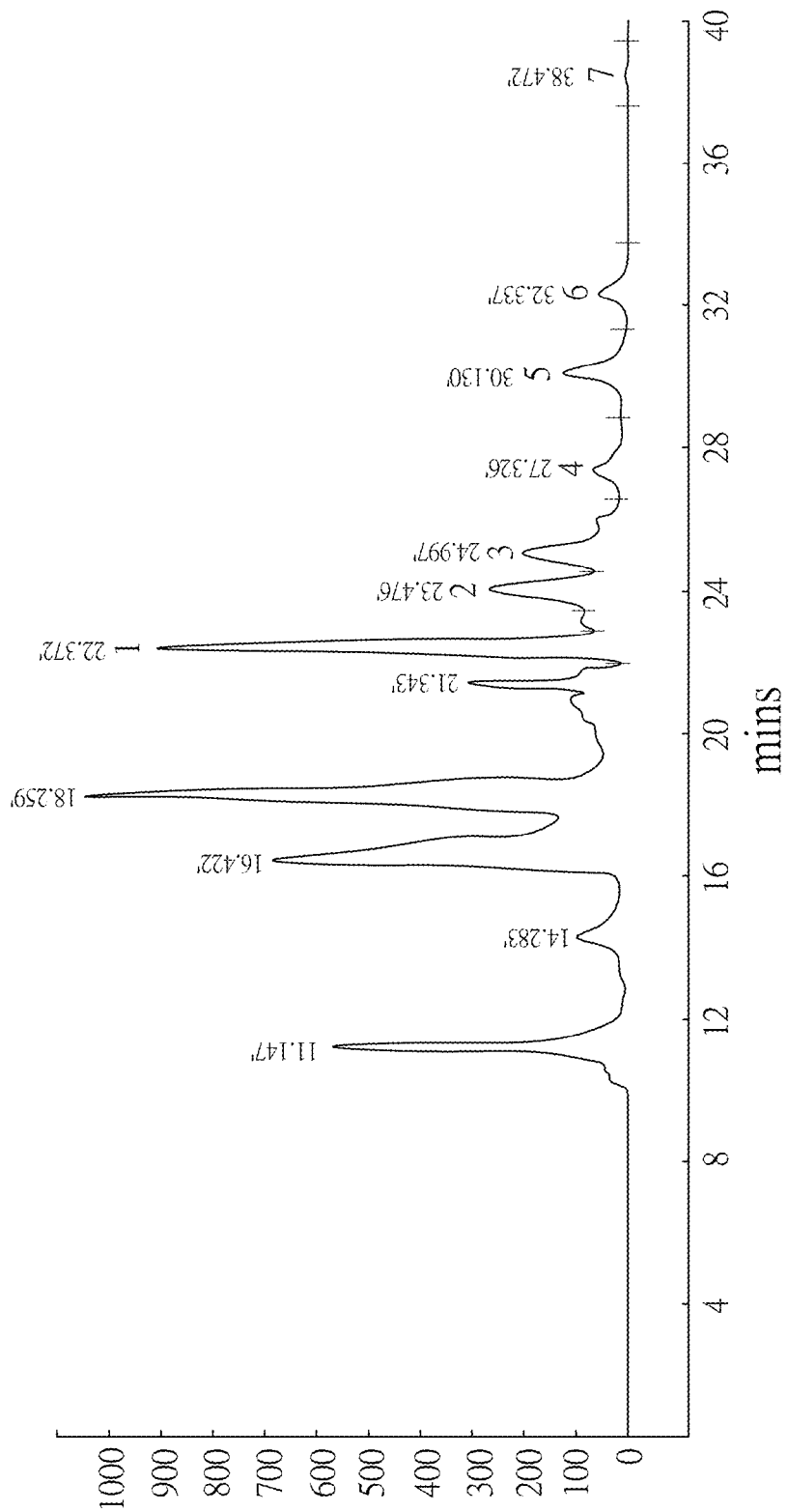
FIG. 17 shows the HPLC chromatogram of the seventh batch of fermented milk.
Figure 18:
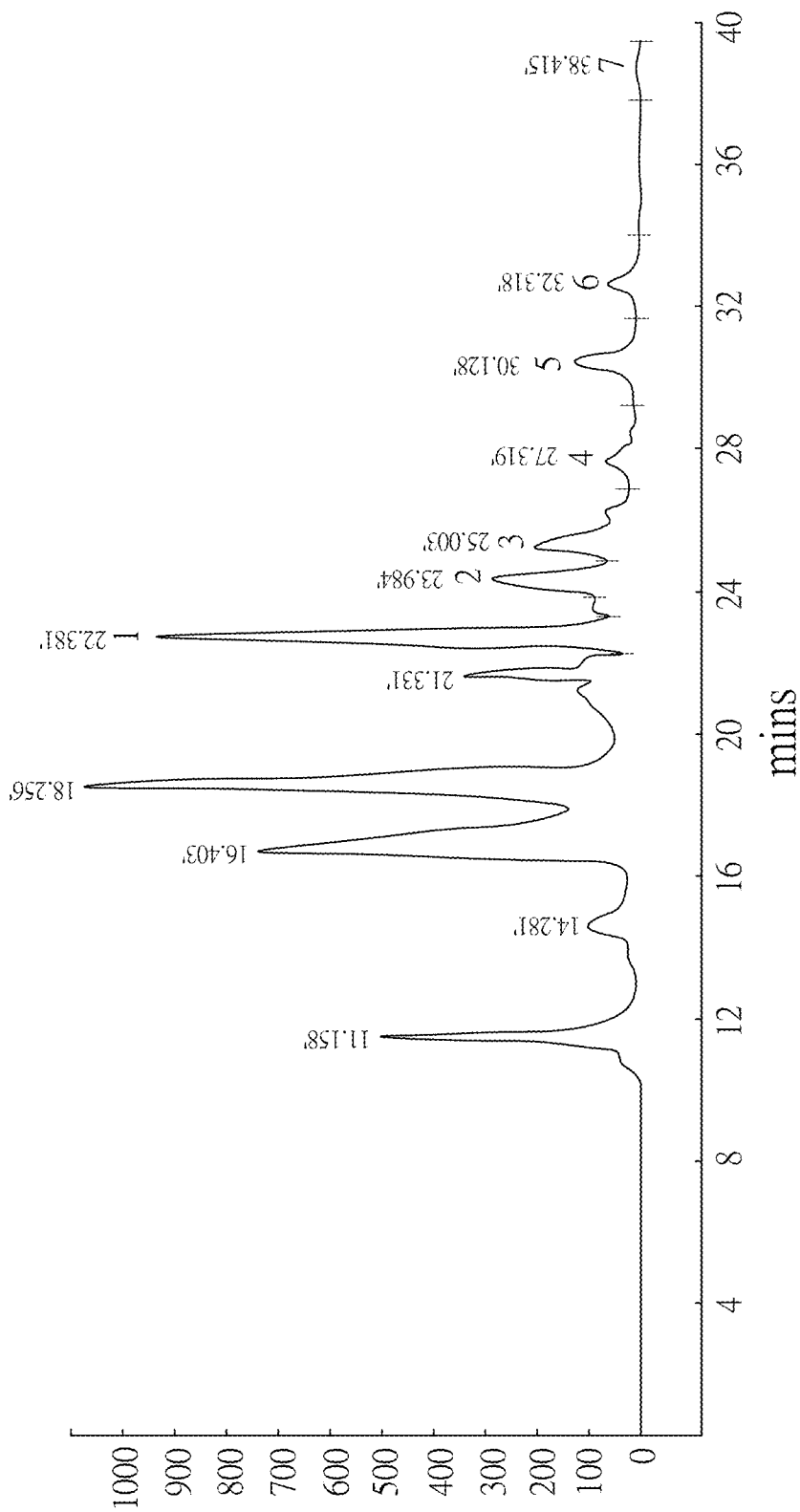
FIG. 18 shows the HPLC chromatogram of the eighth batch of fermented milk.

| | G the retention time for the peaks of reference no. 1 to no. 7 | | | | | | | |
|---|---|---|---|---|---|---|---|---|
| Peak | retention time. ]min.^ | | | | | | | |
| No. | FIG. 11 | FIG. 12 | FIG. 13 | FIG. 14 | FIG. 15 | FIG. 16 | FIG. 17 | FIG. 18 |
| 1 | 21.259 | 22.379 | 22.381 | 22.367 | 22.343 | 22.355 | 22.372 | 22.381 |
| 2 | 22.769 | 23.945 | 23.965 | 23.959 | 23.956 | 23.962 | 23.976 | 23.984 |
| 3 | 23.987 | 24.889 | 24.999 | 24.999 | 25.006 | 25.043 | 24.997 | 25.003 |
| 4 | 25.984 | 27.282 | 27.328 | 27.307 | 27.293 | 27.326 | 27.326 | 27.319 |
| 5 | 28.792 | 30.105 | 30.132 | 30.102 | 30.106 | 30.131 | 30.130 | 30.128 |

TABLE 1-continued

G the retention time for the peaks of reference no. 1 to no. 7

| Peak | retention time. [min. | | | | | | | |
|---|---|---|---|---|---|---|---|---|
| No. | FIG. 11 | FIG. 12 | FIG. 13 | FIG. 14 | FIG. 15 | FIG. 16 | FIG. 17 | FIG. 18 |
| 6 | 30.892 | 32.369 | 32.342 | 32.312 | 32.318 | 32.317 | 32.337 | 32.318 |
| 7 | 36.356 | 38.402 | 38.528 | 38.453 | 38.456 | 38.478 | 38.472 | 38.415 |

EXAMPLE 5

The Peptide Group is Composed of Small Fragmented Peptides

Figure 19:
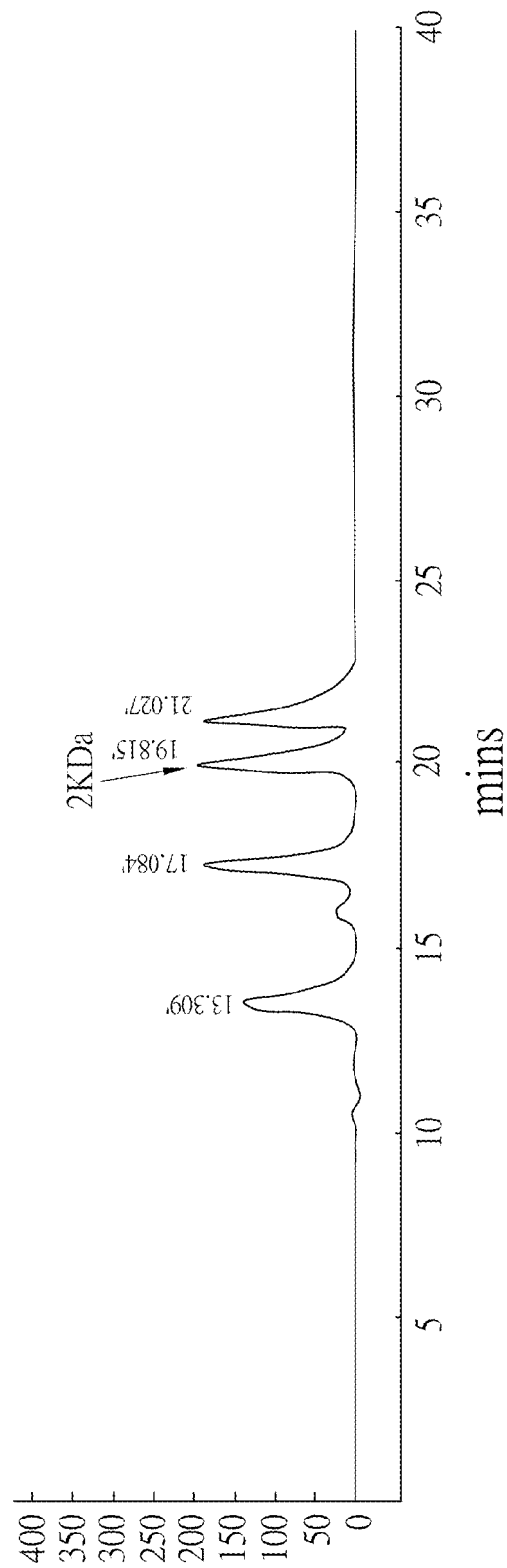
FIG. 19 shows the HPLC chromatogram of the protein standard.

As shown in FIG. 19, a certain amount of the standard protein is separated by HPLC under the same conditions as in Example 4.

Due to the reproducibility of the peptide group such as the peaks of reference no. 1 to no. 7 shown in FIG. 11 to FIG. 18 in the fermented milk, here is taken FIG. 11 for example to compare with the HPLC result of the standard protein. And the result of the comparison is shown in FIG. 20, wherein FIG. 20A and FIG. 20B represent FIG. 11 and FIG. 19 respectively.

Figure 20:
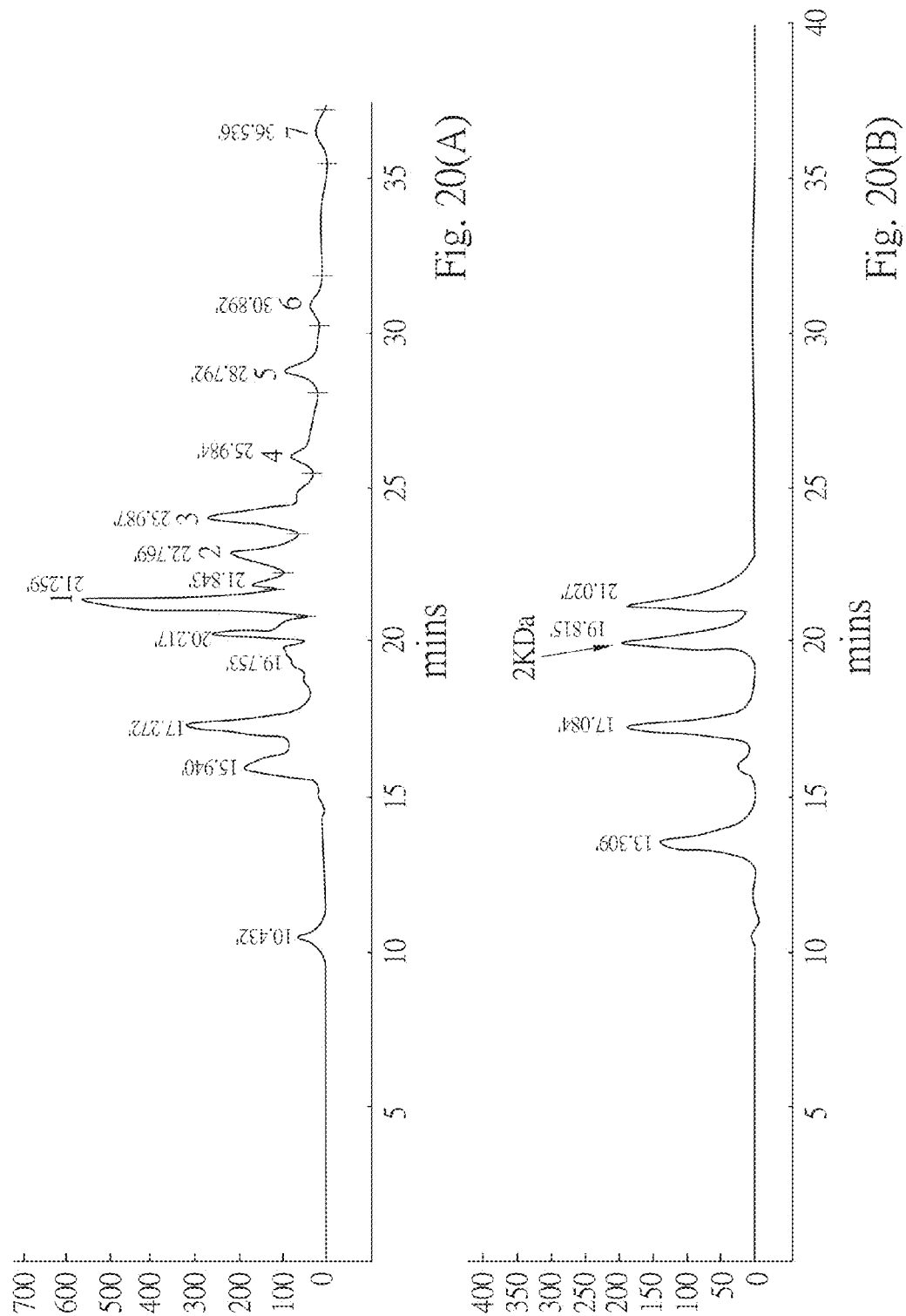
FIG. 20A shows the FIG. 11.
FIG. 20B shows the FIG. 19.

It is indicated the molecular weights of the peptides such as the peaks of reference no. 1 to no. 7 shown in FIG. 20 are all less than 2 kD. In other words, the peptide group from the fermented milk such as the peaks of reference no. 1 to no. 7 shown in FIG. 11 to FIG. 18 is composed of the small fragmented peptides.

EXAMPLE 6

Figure 21:
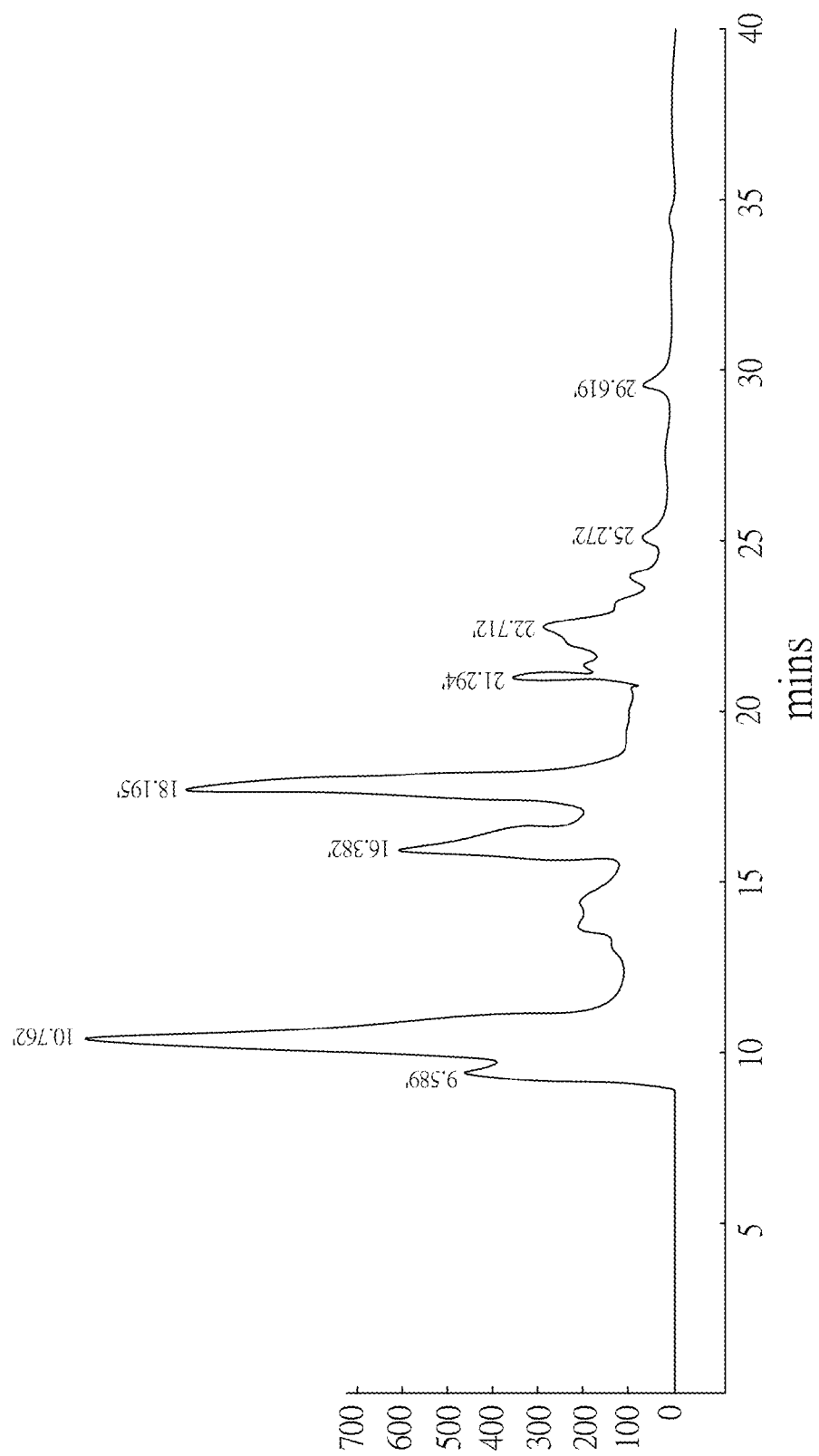
FIG. 21 shows the HPLC chromatogram of the non-fermented material milk.

The Small Fragmented Peptides of Reference No. 1 to No. 7 Shown in FIG. 11 to FIG. 18 Have Anti-Osteoporotic Activity As shown in FIG. 21, a certain amount of non-fermented material milk is separated by HPLC under the same conditions in Example 4.

Due to the reproducibility of the peptide group such as the peaks of reference no. 1 to no. 7 shown in FIG. 11 to FIG. 18 in the fermented milk, here is taken FIG. 12 for example to compare with the HPLC result of the material milk. And the result of the comparison between FIG. 12 and FIG. 21 is shown in FIG. 22, wherein FIG. 22A and FIG. 22B represent FIG. 12 and FIG. 21 respectively.

Moreover, as shown in FIG. 22, the proteins separated from the non-fermented material milk, compared to the fermented milk, are all composed of big molecules, and it doesn't have any small fragmented peptides such as the peaks of reference no. 1 to no. 7 shown in FIG. 22A.

According to the results of Example 4 to Example 6, the small fragmented peptides in the fermented milk such as the peaks of reference no. 1 to no. 7 shown in FIG. 11 to FIG. 18 do not exist in the non-fermented milk. Since the fermented milk can significantly improve osteoporosis and increase bone mineral density, it should be considered that the peptide group such as the peaks of reference no. 1 to no. 7 shown in any one of FIG. 11 to FIG. 18 is with anti-osteoporotic activity.

EXAMPLE 7

The Fermented Milk Processed by Spray Drying Comprises the Peptide Group

In this example, after spray drying the fermented milk, a certain amount of the powdered fermented milk is separated by HPLC under the same conditions in Example 4. And the HPLC chromatograph is shown in FIG. 23.

Figure 23:
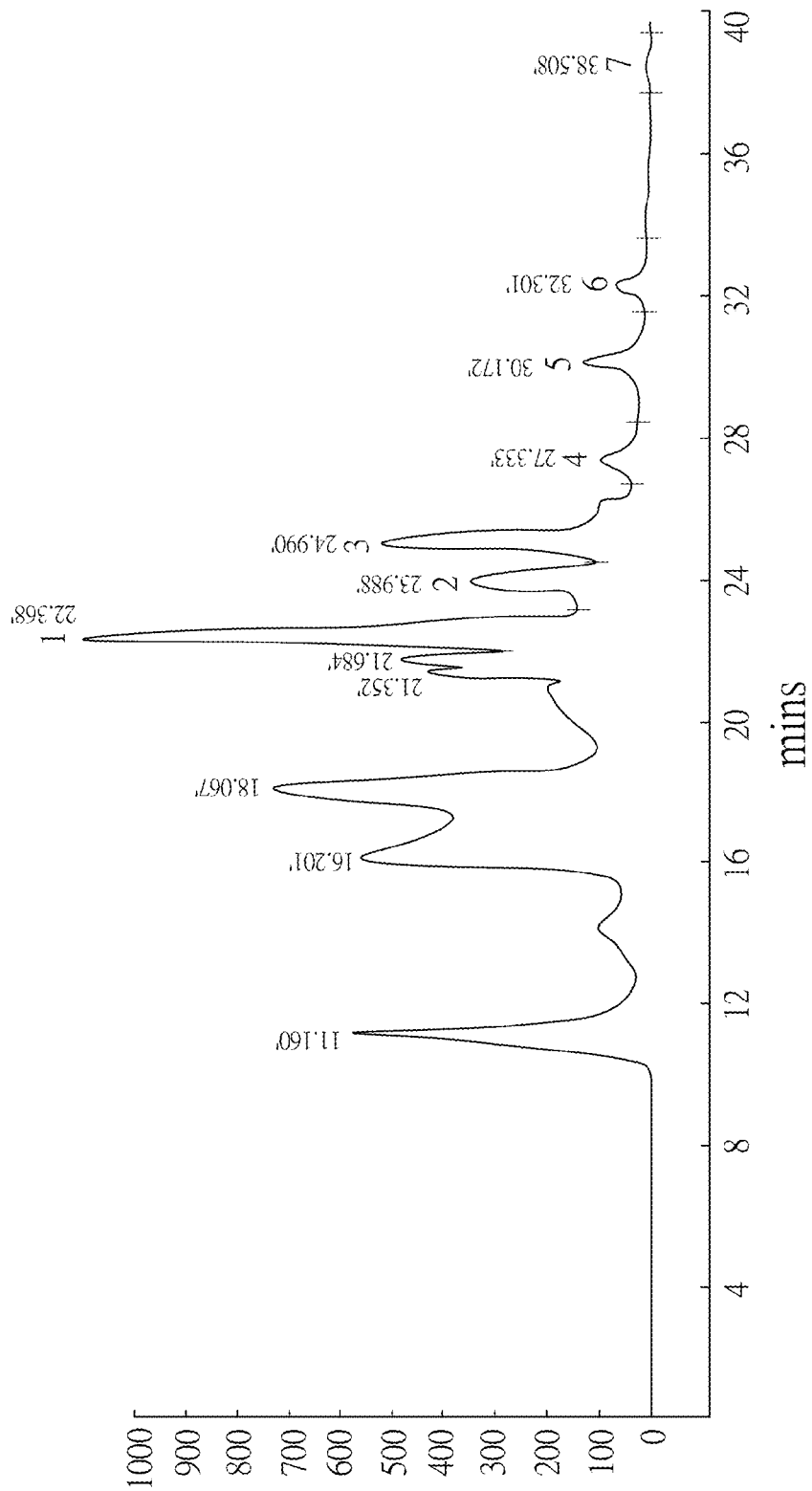
FIG. 23 shows the HPLC chromatogram of the powdered fermented milk.

Since the peptide group such as the peaks of reference no. 1 to no. 7 shown in FIG. 11 to FIG. 18 is presented in the each batch of the fermented milk of Example 2, here is taken FIG. 12 for example to compare with FIG. 23. And the result of the comparison between FIG. 12 and FIG. 23 is shown in FIG. 24, wherein FIG. 24A and FIG. 24B represent FIG. 23 and FIG. 12 respectively.

As shown in FIG. 24, the spray dried fermented milk still contains the small fragmented peptides such as the peaks of reference no. 1 to no. 7 shown in FIG. 11 to FIG. 18. In another word, it is indicated that the small fragmented peptide group will not be destroyed by process of the fermented milk.

Taking all examples described above together, the inventors have clearly demonstrated that the novel milk-fermented product at least having a peptide group comprising peaks of reference no. 1 to no. 7 as shown any one of in FIG. 11 to FIG. 18, wherein these peptide group consists of the small fragmented peptides with anti-osteoporotic activity for not only increasing the ratio of bone volume to total tissue volume, bone mineral density and trabecular number but also decreasing trabecular separation/spacing. Furthermore, it still has the above effects after adding calcium to the fermented milk.

The above-mentioned specification is only for details describing the examples of the invention. Thus, without departing from the spirit and the scope of the present invention, any modification or change on the embodiments of the invention or any equivalent thereof by anyone skilled in the art shall fall the protected scope of the present invention.

The invention claimed is:

1. A method of treating osteoporosis in a human in need thereof comprising administering a therapeutically effective amount of a peptide group isolated from the milk of a fermented kefir grain, which as determined by HPLC analysis has a molecular weight of less than 2 kD and a retention time between 20-40 minutes to the human to treat the osteoporosis in said human.

* * * * *